(12) United States Patent
Rutter

(10) Patent No.: US 8,573,218 B2
(45) Date of Patent: Nov. 5, 2013

(54) TRACHEOSTOMY TUBE

(76) Inventor: Michael John Rutter, Cincinnati, OH (US)

(*) Notice: Subject to any disclaimer, the term of this patent is extended or adjusted under 35 U.S.C. 154(b) by 1527 days.

(21) Appl. No.: 11/683,173

(22) Filed: Mar. 7, 2007

(65) Prior Publication Data

US 2008/0216839 A1   Sep. 11, 2008

(51) Int. Cl.
*A61M 16/04* (2006.01)
(52) U.S. Cl.
USPC ............. 128/207.14; 128/200.26; 128/200.24
(58) Field of Classification Search
USPC ............... 128/207.14, 200.26, 200.24; 623/9; 604/256, 523–539, 93.01, 95.02, 118, 604/264, 258, 94.01, 284
See application file for complete search history.

(56) References Cited

U.S. PATENT DOCUMENTS

| | | | |
|---|---|---|---|
| 2,923,299 A | 10/1957 | Blackwood | |
| 3,853,130 A * | 12/1974 | Sheridan | 604/171 |
| 3,862,635 A * | 1/1975 | Harautuneian | 128/207.15 |
| 4,050,466 A | 9/1977 | Koerbacher | |
| 4,340,046 A | 7/1982 | Cox | |
| 4,471,776 A | 9/1984 | Cox | |
| 4,852,564 A | 8/1989 | Sheridan et al. | |
| 4,987,895 A | 1/1991 | Heimlich | |
| 5,040,531 A | 8/1991 | Coleman et al. | |
| 5,143,062 A | 9/1992 | Peckham | |
| 5,222,487 A | 6/1993 | Carr et al. | |
| 5,245,992 A | 9/1993 | Nye | |
| 5,259,376 A | 11/1993 | Bales | |
| 5,546,936 A * | 8/1996 | Virag et al. | 128/207.14 |
| 5,590,647 A | 1/1997 | Nye | |
| 5,819,723 A * | 10/1998 | Joseph | 128/207.14 |
| 5,819,734 A | 10/1998 | Deiley et al. | |
| 5,877,243 A | 3/1999 | Sarangapani | |
| 5,902,283 A | 5/1999 | Darouiche et al. | |
| 5,983,895 A | 11/1999 | Turner | |
| 6,019,753 A | 2/2000 | Pagan | |
| 6,024,730 A | 2/2000 | Pagan | |
| 6,568,393 B2 * | 5/2003 | Christopher | 128/207.14 |
| 6,575,158 B1 * | 6/2003 | Chelly et al. | 128/200.26 |
| 6,612,305 B2 | 9/2003 | Fauza | |
| 7,087,661 B1 | 8/2006 | Alberte et al. | |
| 7,140,369 B2 | 11/2006 | Rutter | |
| 7,151,139 B2 | 12/2006 | Tiller et al. | |
| 7,601,138 B2 * | 10/2009 | Goebel et al. | 604/158 |

* cited by examiner

*Primary Examiner* — Annette Dixon
(74) *Attorney, Agent, or Firm* — Hasse & Nesbitt LLC; Ronald J. Richter; Donald E. Hasse

(57) ABSTRACT

An improved tracheostomy tube providing a decreased tendency to produce rubbing, pressure necrosis, ulceration and scarring of the tracheal mucosa. The tube typically includes a rigid proximal section, a flexible intermediate section, a rigid distal section, and a beveled distal tip. The flexible intermediate section has a smooth surface and bends easily in response to pressure asserted by the tracheal walls, allowing the distal rigid section of the tube to remain in a parallel orientation relative to the tracheal lumen. The distal tip of the tube is beveled to provide a greater cross-sectional area at the tube's distal section. This beveled distal tip prevents the distal section of the tube from becoming obstructed by the back wall of the trachea or causing erosion of the tracheal mucosa. The distal tip also has a beaded or rounded edge, which further minimizes the risk of damage to the tracheal mucosa and provides a guide to the clinical care specialist during suctioning.

12 Claims, 2 Drawing Sheets

TRACHEOSTOMY TUBE

FIELD OF THE INVENTION

The invention relates generally to medical and surgical devices and in particular to a tracheostomy tube with a flexible mid-shaft design.

BACKGROUND OF THE INVENTION

The human body is far too complicated to be easily replaced by artificial parts, and the upper airway is no exception. The upper airway performs a multitude of functions, the simplest being that of a conduit from the atmosphere to the lungs. Other important functions of the upper airway include humidification and filtration of air, mounting of an immune response to outside infectious agents, removal of debris by deglutition (swallowing) and expectoration (spitting), and speech.

Tracheal tubes are artificial conduits which are commonly inserted into an individual's trachea to enable them to breathe, or to deliver anesthetic gases to an unconscious patient. Tracheal tubes are often required to artificially ventilate an individual in critical clinical situations. While helpful to secure airways and save lives, tracheal tubes can interfere with the other important upper airway functions of the trachea. If they are needed for an extended period of time, tracheal tubes can also be destructive to the surrounding tissues and organs.

Tracheal tubes include both tracheostomy tubes and endotracheal tubes. A tracheostomy tube is inserted through a surgically produced opening in the anterior neck (i.e. through a tracheotomy). An endotracheal tube is inserted into the trachea through the mouth or nose, and is usually formed without a sharp bend, but otherwise is substantially similar to the tracheostomy tube.

Currently tracheostomy tubes come as either a pre-curved tube or a malleable tube that curves once inserted. The disadvantage of a pre-curved tube is that the curve may not suit an individual's particular anatomy, and therefore the tip of the tube may impinge upon the anterior or posterior wall of the trachea. In some individuals, flexion and extension of the neck may also contribute to the tip of the tube impinging on the tracheal wall. The disadvantage of a flexible tube is that the default shape of the tube is straight, and although it will conform to the curve of the tracheostomy tract, it will have a tendency to impinge the posterior wall of the trachea.

One fundamental dilemma common to all tracheal tube designs is that they must have at least some rigidity in order not to kink or collapse, otherwise they are not effective conduits for air, yet they must be gentle on the airway structures. Unfortunately, the rigidity of the tubes invariably causes some force to be applied to the mucosa of the trachea. Tracheal tubes routinely exert pressures far in excess of the mucosal perfusion pressure at the points of contact with the mucosa, such that blood flow, oxygen delivery and waste removal at the points of contact are diminished.

Even despite devoted clinical care, tracheal tubes routinely result in ischemic areas of the tracheal mucosa. Indeed, the complications associated with prolonged intubation can be particularly severe. Persistent irritation of the cartilaginous support of the trachea causes destruction of structures. Later, scarring and stricture formation will result within the trachea once the irritation is removed. Ischemia routinely results in pressure necrosis, ulceration, granulation formation and scarring of the tracheal mucosa. Long term use of a tracheostomy tube often leads to suprastomal granulation tissue formation, suprastomal collapse, and tracheal wall erosion due to the tip of the tube impinging on the interior tracheal wall. As a result, chronic laryngotracheal stenosis can result (which may require a permanent tracheostomy), as well as tracheomalacia, formation of fistulae between the trachea and the esophagus, and erosion of the innominate artery next to the trachea.

In individuals with tracheomalacia, a mobile trachealis (a muscle along the back wall of the trachea) may bulge anteriorly and partly occlude the open distal end of a tracheal tube. This problem arises because the open distal ends of currently used tracheostomy tubes have tips that are cut flush at a 90° angle to the shaft. A secondary problem that arises at the distal end of the tube is that deep suctioning of secretions through the tube may cause damage (granulation or stenosis) to the trachea and bronchi. This occurs because the suction catheter used to perform this maneuver is typically unknowingly extended past the tip of the tube and makes contact with the tracheal and bronchial surfaces, thereby causing the damage.

There exists tracheostomy tubes in the prior art which are designed to minimize damage to the tracheal mucosa. For example, U.S. Pat. No. 4,340,046 to Cox provides a flexible, corrugated, unitary tracheostomy tube. The flexibility so provided is intended to allow the tube to follow lateral movements of the head and neck without significant resistance to those movements, and to adapt to the contour of the neck and trachea. This serves to prevent the end of the tube from scraping the tracheal wall as severely as a more rigid tracheal tube does. U.S. Pat. No. 4,987,895 to Heimlich discloses a tracheostomy tube with a corrugated, flexible and collapsible middle section which allows the tube to elongate and contract during swallowing and respiration in an attempt to reduce rubbing of the tube against the tracheal wall. The tip of the Heimlich tube is intended to remain in a constant position relative to the tracheal mucosa it lies against. In theory this will limit the "rubbing" of the mucosa by either the tip or the cuff of the tracheostomy tube.

While prior art tracheostomy tubes may be useful for their intended purpose, there still exists a need for a tracheostomy tube for patients suffering from tracheomalacia which causes less ischemic areas of the tracheal mucosa, resulting in a decreased tendency to produce rubbing, pressure necrosis, ulceration and scarring of the tracheal mucosa.

SUMMARY OF THE INVENTION

The present invention provides an improved tracheostomy tube with a rigid proximal section, a flexible mid-section, and a rigid distal section. In a preferred embodiment, the tip of the tube does not tend to rub the anterior or the posterior wall of the trachea. The flexible middle section typically has a smooth surface and bends within the trachea and allows the distal rigid section of the tracheotomy tube to lie reasonably parallel with the lumen of the section of the trachea within which it resides. The tube of the invention a so includes a modified tip design with a beveled end to provide a greater cross-sectional area at the tube's distal end and to prevent distal occlusion of the tube by the tracheal walls. The tube can also include a beaded or rounded edge within the tip of the distal shaft to minimize the risk of damage to the mucosa and also to provide a guide to the clinical care specialist when suctioning the distal section of the tube.

A first aspect of the invention provides a tracheostomy tube comprising: a rigid proximal section adapted to connect to a mechanical ventilation device; a flexible intermediate section being bendable along its length; and a rigid distal section including a beveled distal tip adapted to prevent occlusion of the distal section by the tracheal walls, wherein the flexible intermediate section is adapted to bend within the trachea to allow the rigid distal section of the tube to remain in a parallel orientation relative to the tracheal lumen, and wherein the beveled distal tip includes an anterior aspect and a posterior aspect, the anterior aspect being shorter in length than the posterior aspect.

A second aspect of the invention provides a tracheostomy tube comprising: a rigid proximal section adapted to connect to a mechanical ventilation device; a flexible intermediate section being bendable along its length and comprising a smooth surface; and a rigid distal section, wherein the flexible intermediate section is adapted to bend within the trachea to allow the rigid distal section of the tube to remain in a parallel orientation relative to the tracheal lumen, and wherein the proximal section, the intermediate section and the distal section are each sufficiently rigid to resist collapse in the radial direction.

A third aspect of the invention provides a tracheostomy tube comprising: a beveled distal tip adapted to prevent distal occlusion of the tube by the tracheal walls, the beveled distal tip including an anterior aspect and a posterior aspect, the anterior aspect being shorter in length than the posterior aspect.

The nature and advantages of the present invention will be more fully appreciated from the following drawings, detailed description and claims.

BRIEF DESCRIPTION OF THE DRAWINGS

The accompanying drawings illustrate embodiments of the invention and, together with a general description of the invention given above, and the detailed description given below, serve to explain the principles of the invention.

DETAILED DESCRIPTION OF THE INVENTION

The tracheostomy tube of the invention is intended for use in children and adults with tracheomalacia, as well as in children and adults in whom the tip of the tracheotomy tube is prone to become either partly obstructed within the trachea, or is at risk of causing mucosal damage. The intermediate section of the tube is flexible, which allows the distal section of the tube to safely move within the trachea as the trachea moves. The tip of the tube, at its distal section, typically includes a beveled end with a large cross-sectional area, whereby the posterior aspect of the distal shaft is longer than the anterior aspect of the distal shaft. The tube thus does not have a tendency to become obstructed at its distal end, or cause erosion of the tracheal mucosa, as do prior art tubes.

Figure 1:
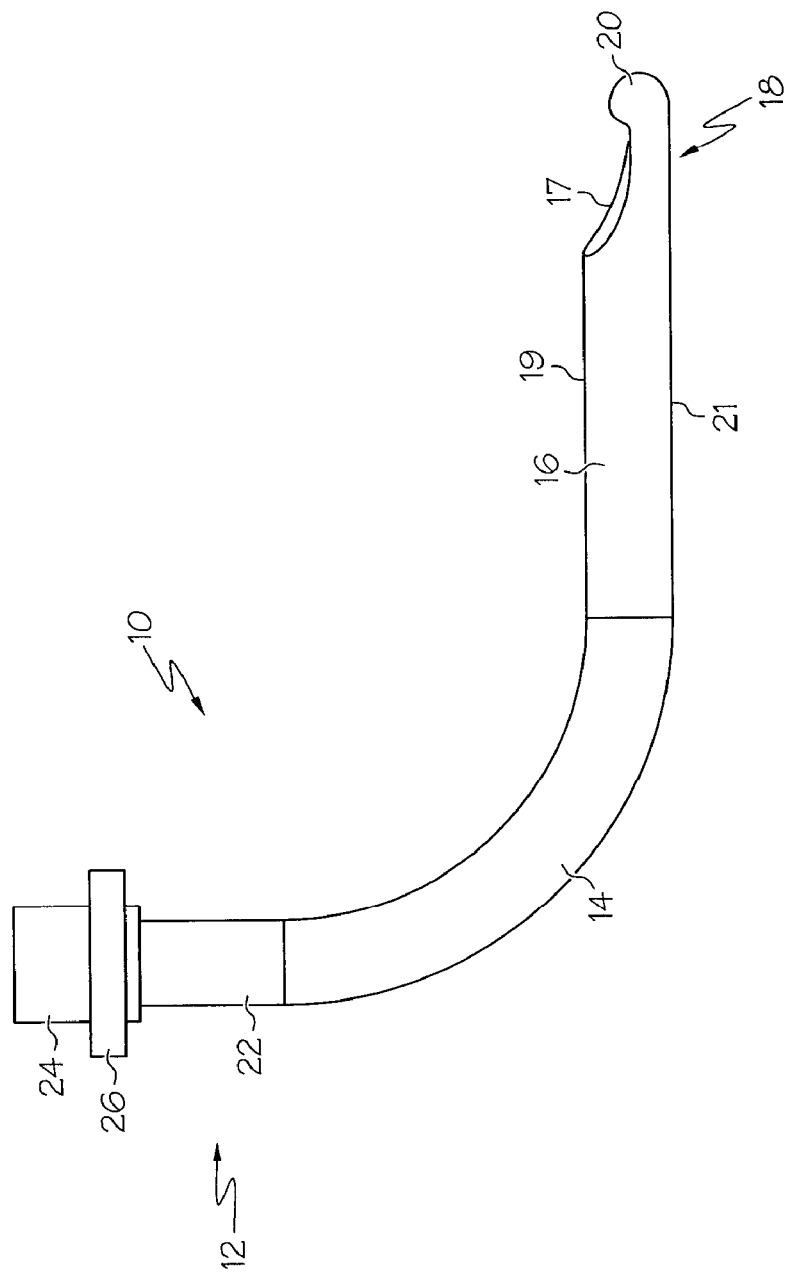
FIG. 1 is a plan view of one embodiment of the present invention.

FIG. 1 is a plan view according to a first embodiment of the present invention. In particular, FIG. 1 shows a tracheostomy tube 10 having a proximal or machine end section 12. A flexible intermediate section 14 connects the proximal section 12 to a distal or patient end section 16 along the length of the tube. The distal section 14 terminates in a beveled distal tip 18 having an outlet orifice 17. The beveled distal tip 18 is intended to create an outlet orifice with a large cross-sectional area, in order to decrease the chances of the outlet orifice 17 becoming occluded by the tracheal walls of a patient with tracheomalacia, which is a common problem seen with prior art tubes. Thus, the anterior aspect 19 of the distal section 16 is much shorter in length than its posterior aspect 21. As a non-limiting example, the anterior aspect 19 is typically about 1 mm to about 3 mm shorter in length than the posterior aspect 21. A rounded or beaded edge 20 is typically located at the distal-most part of the posterior aspect 21 of the distal section 16, in order to minimize the risk of damage that such a "pointed" tip may cause. This beaded edge also performs the function of alerting a care provider suctioning the tracheotomy tube that the suction catheter has reached the end of the tube, thereby minimizing the risk of tracheal or bronchial mucosal damage from deep suctioning.

The proximal section 12 of the tube 10 comprises a curved, rigid shaft portion 22 which enters the trachea through the tracheostomy site. The shaft portion 22 terminates proximally in an inlet orifice adapted to receive a standard connector 24, which is typically adapted to connect to any suitable connectors and/or adapters for attachment to an anesthesia machine, a mechanical ventilation device, or the like. The connector 24 can also include lateral flanges 26 for the attachment of tracheotomy ties for securing the tube about the neck of an individual. The shaft portion 22 of the proximal section 12 is typically curved to accommodate ergonomic placement of the tube within the tracheostomy site. The connector 24 is typically a 15 mm ISO connector.

The shaft portion 22 of the proximal section 12 is typically of a fixed length which is typically determined by the inner diameter of the tube, and has an outside diameter and inner diameter equivalent to that of the intermediate section 14 and the distal section 16. More specifically, the proximal section 12 may vary in length from about 4 mm to about 8 mm for a tracheotomy tube with an inner diameter of 2.5 mm, through to a length of about 10 mm to about 25 mm for a tracheotomy tube with an inner diameter of 9.0 mm.

The distal section 16 and the proximal section 12 are each attached to the flexible intermediate section 14, which is also typically of a fixed length and has outer and inner diameters equivalent to the outer and inner diameters of both the distal section 16 and the proximal section 12. In the event that the wall thickness of the flexible intermediate section 14 is greater that of the proximal section 12 and the distal section 16, then the inner diameter of the intermediate section 12 is typically the same as sections 12 and 16, while the outer diameter would be greater. The typical length of the flexible intermediate section 14 typically varies from between about 10 mm to about 15 mm for a tracheotomy tube with a 2.5 mm inner diameter, through to about 20 mm to about 40 mm for a tracheotomy tube with a 9.0 mm inner diameter.

The length of the distal section 16 is variable, but typically ranges from between about 8 mm to about 60 mm in length, and may be customized to meet the needs of an individual patient. The various tubing portions of the tracheal tube according to the present invention should have the same inside and outside diameters. Suitable inside diameters range from 2.5 mm to 9.0 mm, with corresponding outside diameters ranging from 4.0 mm to 12.5 mm. The intermediate section 14 can be attached to the distal section 16 and the proximal section 12 by any suitable means, such as adhesives, connectors, compression fittings, or inserted molded connectors, as are known in the art. As a non-limiting example, a connector can be used such as that disclosed in U.S. Pat. No. 5,590,647 to Nye, to connect the intermediate section 14 to the distal section 16 and the proximal section 12.

The proximal section 12 and the distal section 16 of tracheal tube 10 may be preformed from any suitable material having sufficient resilience such that these sections retain their configuration and do not kink during use. Flexible thermoplastic materials such as polyvinylchloride, polyethylene, or the like are preferred materials meeting all of the above requirements.

The material forming the intermediate section 14 resists kinking and bends easily. By providing such a flexible intermediate section 14 which easily bends in response to outside pressure, the rigid distal section 16 of the tube typically remains in a parallel orientation relative to the tracheal lumen even though the intermediate section 14 is in bending motion. Movement of the intermediate section also typically occurs without a large corresponding movement of the proximal section 12. Further, the trachea of a patient can move up and down during swallowing, breathing, coughing, etc., and slide over the intermediate section 14 and distal section 16 without producing undue stress on the tracheal walls.

The flexible intermediate section 14 may be formed of any suitable flexible material which allows for easy bending in response to movement of (or contact with) the trachea during swallowing or coughing while maintaining constant connection to the proximal and distal sections 12, 16 of the tracheal tube 10. This material must be capable of easily bending without kinking or transferring unnecessary force to the proximal section 12 or the distal section 16, while maintaining constant inside and outside diameters. In a preferred embodiment, the flexible intermediate section 14 is formed from either expanded polytetrafluoroethylene (PTFE, Teflon) tubing or a polyethylene material (any grade).

Unlike some prior art tubes, in which the intermediate portion is designed to elongate and contract with the trachea during swallowing and respiration, the intermediate section of the tube of the invention bends easily while allowing the rigid distal section of the tube to remain in a parallel orientation relative to the tracheal lumen so that the tip of the tube does not rub the anterior or posterior walls of the trachea. This allows the tip of the tube to orient within the trachea to its best anatomical advantage for any given individual, and therefore the risk of injury or trauma to the patient's mucosa and trachea may be minimized. Further, the smooth surface of the intermediate section allows the trachea to move up and down and slide over the intermediate section of the tube without irritation during swallowing and respiration. In a preferred embodiment of the tube of the invention, all sections of the tube 10, i.e. the proximal section 12, the intermediate section 14 and the distal section 16, are each smooth on their surface and sufficiently rigid to resist collapse in the radial direction.

Figure 2:
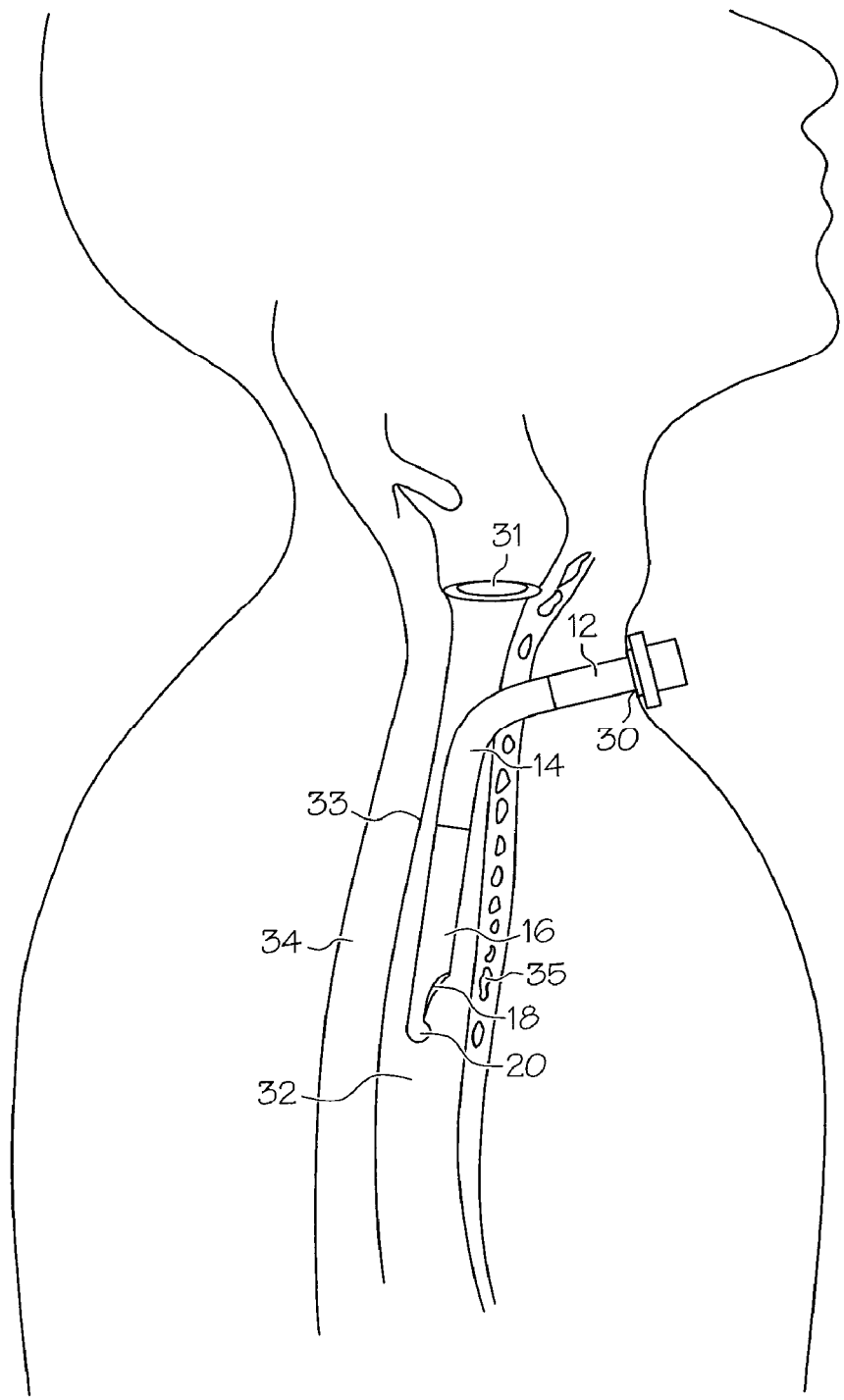
FIG. 2 is a partial longitudinal section of a patient's neck in which a tube of the invention has been inserted.

As illustrated in FIG. 2, the tube of the invention is shown inserted through a tracheostomy site 30 in a patient's neck and into the trachea 32. As shown, the esophagus 34 is located behind the trachea 32, and proper placement of the tube is below the level of the vocal cords 31 in the trachea 32 and between the posterior tracheal wall 33 and the anterior tracheal wall 35. The intermediate section 14 is bendable along its length and has a smooth surface, such that, in use, the bending of the intermediate section 14 within the trachea 32 allows the rigid distal section 16 of the tube to remain in a parallel orientation relative to the tracheal lumen 32, thus being substantially aligned with the patient's trachea without rubbing on the posterior or anterior tracheal walls 33, 35. The smooth surface of the intermediate section 14 typically allows the trachea 32 to slide along its surface during contact, and if pressure is asserted by the trachea walls 33, 35 then the intermediate section 14 will bend away from the direction of force of the tracheal wall without causing trauma, while the attached distal section 16 remains aligned within the tracheal lumen.

Since the distal section 16 typically includes a beveled tip 18 with a large outlet orifice 17 and a beaded edge 20, even if the tip 18 should contact or impinge the posterior tracheal wall 33, or with marked tracheomalacia, occlusion of the distal tip is markedly reduced, if not absent. The beaded edge 20 can also provide a guide to the clinician when suctioning secretions out of the inside of the tube, to indicate that the end of the tube has been reached. Indeed, the beveled distal tip 18 and the beaded edge 20 of the invention can be part of a prior art shaft that does not include the benefit of a flexible intermediate section, to prevent distal occlusion of the tube by the tracheal walls, to minimize the risk of damage to the tracheal walls, and to provide a guide indicating the end of the tube during suctioning.

As is standard in the art, the tracheal tube of the invention can include an inflatable cuff (not shown) mounted on its distal section to aid in positive pressure ventilation. The cuff typically inflates circumferentially around the distal section of the tube. The inflatable cuff typically includes a means for inflation and deflation, such as an inflation tube having an inflation end and a cuff end. Typically the inflation end is connectable to a means for inflating the cuff, such as an air-filled syringe, and the cuff end communicates with the interior of the cuff.

Since it is well-known that endotracheal and tracheostomy tubes act as a reservoir for biofilm formation by infecting microorganisms which exhibit significantly greater antibiotic resistance than their tracheal counterparts, the tube of the invention can also have a surface preparation to minimize the adherence of bacterial biofilm thereon, as is known in the art. For example, various methods have been employed to coat the surfaces of medical devices with antibiotics and other bacteriostatic compounds (See e.g. U.S. Pat. Nos. 5,877,243, 5,902,283, 7,087,661 and 7,151,139).

Although various embodiments of the invention have been described and exemplified, it will be understood that the scope of the invention is not limited to that description. Changes and modifications will occur to those of ordinary skill in the art and they can be made without departing from the spirit and scope of the invention. The invention is considered to include the methods of accomplishing the results described herein as well as structures designed to accomplish them.

What is claimed is:

1. A tracheostomy tube comprising:
   a rigid proximal section adapted to connect to a mechanical ventilation device;
   a flexible intermediate section being bendable along its length and insertable below the vocal cords in the trachea; and
   a rigid distal section including a beveled distal tip adapted to prevent occlusion of the distal section by the tracheal walls,
   wherein the flexible intermediate section does not elongate or contract in the axial direction, and bends in response to outside pressure exerted during swallowing or coughing to allow the rigid distal section of the tube to move within the trachea and remain in a parallel orientation relative to the tracheal lumen, and wherein the beveled distal tip includes an anterior aspect and a posterior aspect, the anterior aspect being shorter in length than the posterior aspect.

2. The tracheostomy tube of claim 1, wherein the anterior aspect of the beveled distal tip is between 1 mm to 3 mm shorter in length than the posterior aspect.

3. The tracheostomy tube of claim 1, wherein the posterior aspect of the distal tip includes a rounded, beaded edge adapted to minimize the risk of damage to the tracheal walls and to provide a guide indicating the end of the tube during suctioning.

4. The tracheostomy tube of claim 1, wherein the proximal section, the intermediate section and the distal section are each sufficiently rigid to resist collapse in the radial direction.

5. The tracheostomy tube of claim 1, wherein the proximal section, the intermediate section and the distal section each comprise a smooth surface.

6. A tracheostomy tube comprising:
a rigid proximal section adapted to connect to a mechanical ventilation device;
a flexible intermediate section being bendable along its length, insertable below the vocal cords in the trachea, and comprising a smooth surface; and
a rigid distal section,
wherein the flexible intermediate section does not elongate or contract in the axial direction, and bends in response to outside pressure exerted during swallowing or coughing to allow the rigid distal section of the tube to move within the trachea and remain in a parallel orientation relative to the tracheal lumen, and wherein the proximal section, the intermediate section and the distal section are each sufficiently rigid to resist collapse in the radial direction.

7. The tracheostomy tube of claim 6, wherein the distal section comprises a beveled distal tip, the beveled distal tip adapted to prevent occlusion of the distal section by the tracheal walls and including an anterior aspect and a posterior aspect, the anterior aspect being shorter in length than the posterior aspect.

8. The tracheostomy tube of claim 7, wherein the anterior aspect of the distal tip is between 1 mm to 3 mm shorter in length than the posterior aspect.

9. The tracheostomy tube of claim 7, wherein the posterior aspect of the distal tip includes a rounded, beaded edge adapted to minimize the risk of damage to the tracheal walls and to provide a guide indicating the end of the tube during suctioning.

10. A tracheostomy tube comprising: a rigid proximal section
adapted to connect to a mechanical ventilation device;
a flexible intermediate section being bendable along its length and insertable below the vocal cords in the trachea; and
a rigid distal section including a beveled distal tip adapted to prevent distal occlusion of the tube by the tracheal walls, the beveled distal tip including an anterior aspect and a posterior aspect, the anterior aspect being shorter in length than the posterior aspect, wherein the posterior aspect of the distal tip includes a rounded, beaded edge to minimize the risk of damage to the tracheal walls and to provide a guide indicating the end of the tube during suctioning, wherein
wherein the flexible intermediate section does not elongate or contract in the axial direction, and bends in response to outside pressure exerted during swallowing or coughing to allow the rigid distal section of the tube to move within the trachea and remain in a parallel orientation relative to the tracheal lumen.

11. The tracheostomy tube of claim 10, wherein the anterior aspect of the distal tip is between 1 mm to 3 mm shorter in length than the posterior aspect.

12. The tracheostomy tube of claim 10, wherein the proximal section, the intermediate section and the distal section each comprise a smooth surface and are each sufficiently rigid to resist collapse in the radial direction.

* * * * *